United States Patent [19]

Kamahori

[11] Patent Number: 5,480,614

[45] Date of Patent: Jan. 2, 1996

[54] MICRO-REACTOR DEVICE FOR MINUTE SAMPLE ANALYSIS

[75] Inventor: Masao Kamahori, Saitama, Japan

[73] Assignee: Hitachi, Ltd., Tokyo, Japan

[21] Appl. No.: 213,526

[22] Filed: Mar. 16, 1994

[30] Foreign Application Priority Data

Mar. 16, 1993 [JP] Japan .................................. 5-055327

[51] Int. Cl.[6] .......................... G01N 27/30; G01N 27/447
[52] U.S. Cl. .............................. 422/70; 422/50; 422/68.1;
422/81; 422/82.05; 422/108; 422/116; 422/145;
422/213; 436/52; 436/150; 436/806; 204/299 R
[58] Field of Search ................................ 422/50, 58, 70,
422/68.1, 73, 81, 82.05, 102, 104, 108,
116, 145, 211, 213; 436/52, 178, 150, 806,
533, 541; 204/299 R

[56] References Cited

U.S. PATENT DOCUMENTS

| | | | |
|---|---|---|---|
| 4,729,947 | 3/1988 | Middendorf et al. | 435/6 |
| 4,882,127 | 11/1989 | Rosenthal et al. | 422/50 |
| 4,908,112 | 3/1990 | Pace | 204/299 R |
| 5,100,627 | 3/1992 | Buican et al. | 422/108 |
| 5,149,661 | 9/1992 | Gjerde et al. | 436/178 |
| 5,171,989 | 12/1992 | Williams et al. | 250/288 |

FOREIGN PATENT DOCUMENTS

| | | |
|---|---|---|
| 0081116A1 | 6/1983 | European Pat. Off. . |
| 0081116 | 6/1983 | European Pat. Off. . |
| 3523558A1 | 1/1987 | Germany . |
| 4105107A1 | 9/1991 | Germany . |
| 4-221764 | 8/1992 | Japan . |
| 9115758 | 10/1991 | WIPO . |
| WO91/15750 | 10/1991 | WIPO . |

OTHER PUBLICATIONS

Wu et al, Capillary Zone Electrophoresis . . . Amino Acids, Feb. 24, 1992, Talanta, vol. 39, No. 2, pp. 173–178.
Bruno et al, Thermo–Optical Absorption Detection in 25-μm-i.d Capillaries–Capillary . . . Mixtures, Applied Spectroscopy, vol. 45, No. 3, 1991 pp. 462–467.
Yu et al, Attomole Amino Acid Determination by Capillary Zone Electrophoresis With Thermooptical Absorbance Detection Analytical Chemistry, vol. 61, No. 1, Jan. 1, 1989, pp. 37–40.
Sensors and Actuators B, vol. 10, pp. 107–116, 1993, D. Jed Harrison, et al., "Towards miniaturized electrophoresis and chemical analysis systems on silicon: an alternative to chemical sensors".
Anal. Chem., vol. 65, pp. 1481–1488, 1993, Kurt Seiler, et al., "Planar Glass Chips for Capillary Electrophoresis: Repetitive Sample Injection, Quantitation, and Separation Efficiency".
Anal. Chem., vol. 65, pp. 2637–2642, 1993, Carlo S. Effenhauser, et al., "Glass Chips for High-Speed Capillary Electrophoresis Separations with Submicrometer Plate Heights".
"A Gas Chromatographic Air Analyzer Fabricated on a Silicon Wafer", Terry et al, IEEE Transactions on Electron Devices, vol. ED-26, No. 12, Dec. 1979, pp. 1880–1886.

Primary Examiner—James C. Housel
Assistant Examiner—Harold Y. Pyon
Attorney, Agent, or Firm—Antonelli, Terry, Stout & Kraus

[57] ABSTRACT

A minute sample analysis system includes a micro-reactor device, a quantitative measuring device, an analyzing device and a controller, whereby, when a very small amount of sample is handled, its dilution and loss can be suppressed to minimum level, and analyzing operations ranging from reaction with a reactive reagent to separation/detection of the sample can be consistently carried out efficiently. The micro-reactor device controls the solution, reactive reagent and sample flowing in the form of electroosmotic flow generated by high-voltage application under control of passage change-over switches. The quantitative measuring device measures the quantity of reactive sample received from the micro-reactor device and introduces the measured reactive sample into the analyzing device. The analyzing device optically detects components separated from the sample through electrophoresis. The above operations are generally controlled under by the controller.

11 Claims, 8 Drawing Sheets

MICRO-REACTOR DEVICE FOR MINUTE SAMPLE ANALYSIS

BACKGROUND OF THE INVENTION

The present invention relates to a micro-reactor device in which a minute of sample material is made to react in a microscopic area and also to a minute sample analysis system which uses the micro-reactor device.

As a method for causing reaction between sample and reactive reagent on a flow basis, a flow injection analysis is generally applied to the sample which is introduced into the reactive reagent and made to react therewith during flow of the sample liquid and to be subjected to a concentration measurement by an optical detection method based on its abasorbance. Details of such methods which details are shown, for example, in Analytical Chemistry, Vol. 50 (1978), pp. 832A–846A or in Analytical Chemistry, Vol. 53 (1981), pp. 20A–32A or in Analytica Chimica Acta, Vol. 78 (1975), pp. 145–157.

SUMMARY OF THE INVENTION

In the case where a liquid feeding pump of a mechanical drive type is used in the above-mentioned flow injection analysis, flow within a flow passage becomes laminar flow having a flow profile 41 as shown in FIG. 2. The laminar flow has such a velocity distribution that the flow has a velocity of substantially zero at its both ends due to the flow resistance of walls 42 and 43 of the passage and has a maximum velocity at its central part. For this reason, there occurs a problem that such a difference in the flow velocity within the passage causes the injected sample to flow through the passage without keeping its original shape. And consequently, band broadening of the injected sample, as a result of mixing with the solution at its front and rear ends thereof, results in a decrease of concentration of the sample liquid and in an increase of volume in the sample.

In this connection, a pressure drop $\Delta p$ is expressed as a Hagen-Poiseuille law which follows.

$$\Delta p = 8\mu l Q/r^4$$

where $\mu$ denotes the viscosity of the liquid, l denotes the length of the passage, Q denotes flow quantity, and r denotes the radius of the passage.

That is, the pressure drop increases inversely proportional to the fourth power of the radius of the passage. For this reason, when a capillary as small as 100 μm or less is used as the passage for the purpose of handling such a very small amount of sample as a nanoliter level, the pressure drop becomes large, which involves another problem of withstanding pressure within the apparatus. That special measure must be take providing a pressure resistive property to the wall material of the passage and also to a coupling part between the passages.

Thus, there have not been so far realized a micro-reactor device wherein a very small amount of sample as minute as nanoliter level is made to react with reactive reagent, as well as a minute sample analysis system which is a combination of the micro-reactor device for pretreatment and an analyzing device suitable for analysis of a very small amount of sample composition such as a capillary electrophoresis device.

In order to solve the above problems, in accordance with the present invention, transfer of sample and reactive reagent in a micro-reactor device is carried out on an electroosmotic flow.

Further, the micro-reactor device is formed on a planar substrate having very narrow grooves.

Furthermore, the micro-reactor device is coupled via a quantitative measuring device with a capillary electrophoresis device.

Electroosmotic flow takes place when application of a voltage across a capillary tube causes electric double layers 51 and 52 formed on the internal surface of the tube to move in the same direction as an electric field established by an applied voltage, as shown in FIG. 3. In this case, the flow profile is a flat flow 53 as shown in FIG. 3. For this reason, sample diffusion is as small as several tenths of that in the case of laminar flow. A velocity $u_{osm}$ of the electro-osmotic flow is expressed by the following equation.

$$U_{osm} = keE/z\eta\sqrt{c}$$

where, k denotes a constant, e denotes charge quantity of the capillary tube per its unit surface, E denotes applied voltage, z denotes the number of charges in electrolyte, $\eta$ denotes the viscosity of solution, and c denotes the concentration of the electrolyte.

In this way, since the electroosmotic flow depends on the applied voltage, the concentration of the electrolyte in the solution, and the sign and the quantity of charges on the surface of the capillary tube, control of the quantity of solution to be transferred can be facilitated. Further, the pressure drop caused by the solution transfer is substantially zero.

The capillary electrophoresis is an effective analyzing method having a high separation ability but requires the sample quantity to be as small as the nanoliter level. Thus, for the purpose of preventing a large quantity of sample solution from being introduced from the micro-reactor device into the capillary electrophoresis device, there is provided a quantitative measuring device between the capillary electrophoresis device and the micro-reactor device. As a result, a very small amount of sample can be accurately introduced into the capillary electrophoresis device, and on-line analysis, including the reaction of a very small sample with the reagent and separation of sample compositions, can be performed without subjecting to any dilution and loss.

DESCRIPTION OF THE PREFERRED EMBODIMENTS

Figure 1:
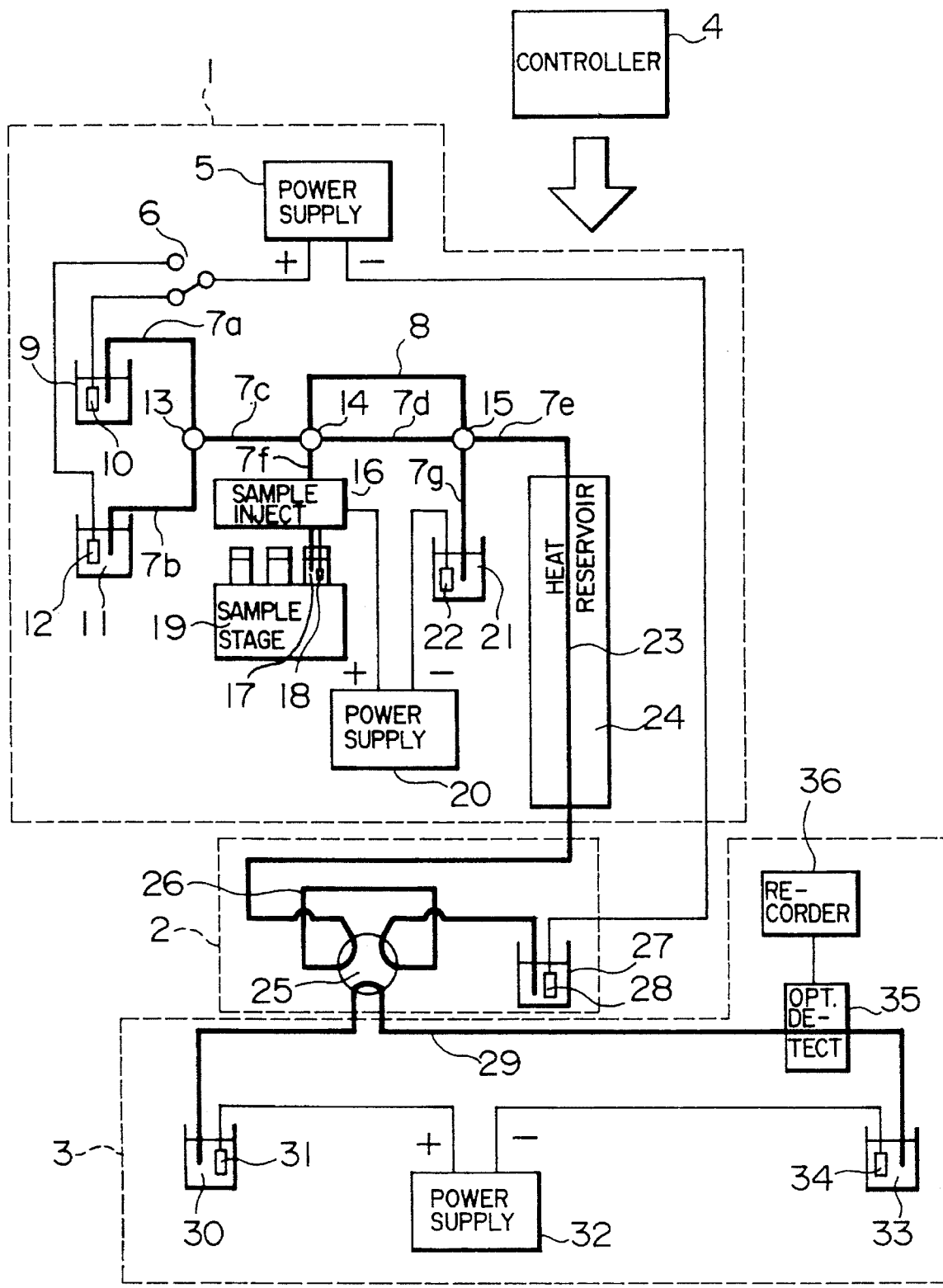
FIG. 1 is a block diagram of an arrangement of a minute sample analysis system in which a first micro-reactor device is used in accordance with the present invention.
Figure 2:
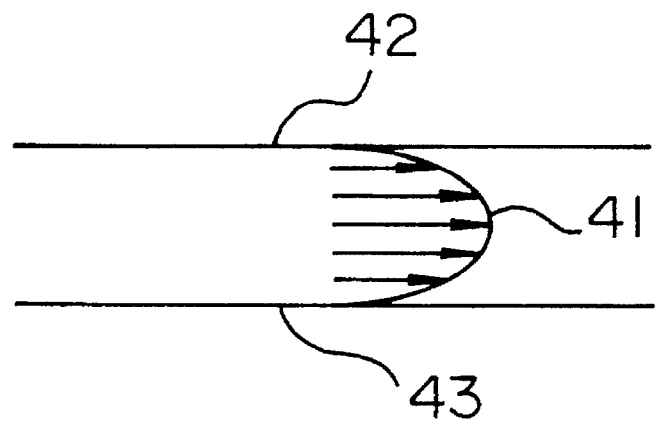
FIG. 2 shows a flow profile of laminar flow.
Figure 3:
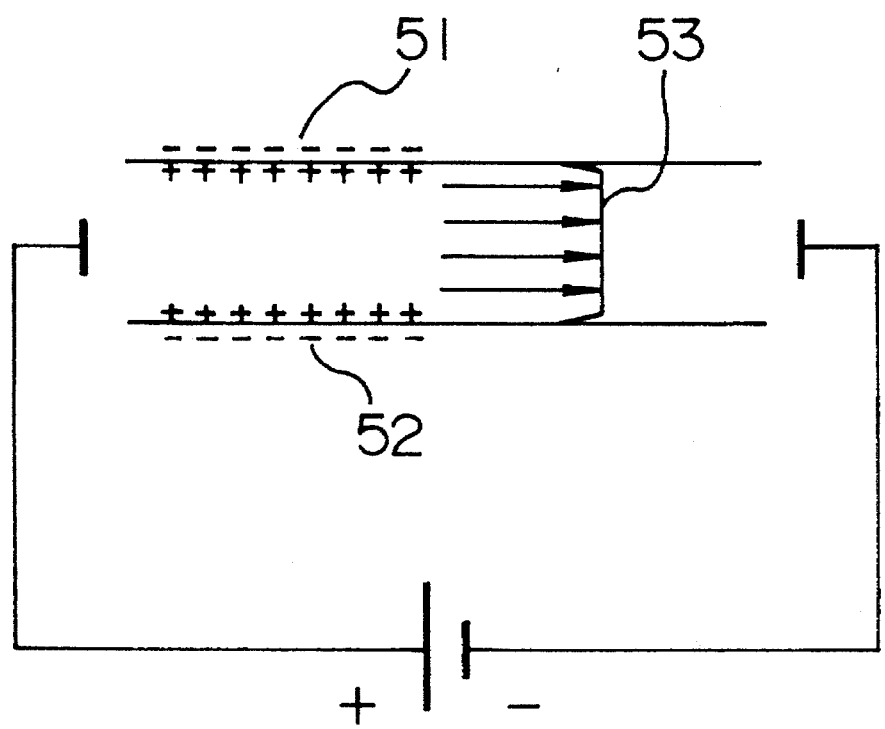
FIG. 3 is a flow profile of electroosmotic flow.

A first embodiment of the present invention will be explained with reference to FIG. 1 showing its block diagram.

A minute sample analysis system of FIG. 1 in accordance with the first embodiment of the present invention comprises a micro-reactor device 1, a quantitative measuring device 2, an analyzing device 3, and a controller 4.

More specifically, the micro-reactor device 1 includes a power supply 5 for liquid transfer; power change-over switch 6; passages 7a to 7g; sample quantity measurer 8; a solution reservoir 9; a reactive reagent reservoir 11; platinum electrodes 10, 12, 18 and 22; passage change-over switches 13, 14 and 15; an automatic sample injector 16, a sample reservoir 17, a sample stage 19, a power supply 20 for sample introduction, a waste solution reservoir 21, a reactor 23, and a constant-temperature heat resevior 24. The micro-reactor 1 functions to provide pre-treatment to cause reaction between sample and such reactive reagent as fluorescent reagent.

The power supply for liquid transfer 5, which comprises a high voltage power supply having an output voltage of 0–30 kV, applies a high voltage between the platinum electrode 10 of the solution reservoir 9 and the platinum electrode 28 of the waste solution reservoir 27 of the quantitative measuring device 2, or to between the platinum electrode 12 of the reactive reagent reservoir 11 and the platinum electrode 28 of the waste solution reservoir 27 of the quantitative measuring device 2. An eluting solution within the solution reservoir 9, when the high voltage is applied between the solution reservoir 9 and the waste solution reservoir 27 of the quantitative measuring device 2, is circulated in the form of an electroosmotic flow, caused by the high voltage application, through the passages 7a, 7c, 7d and 7e sequentially in this order. Similarly, a reactive reagent solution within the reactive reagent reservoir 11, when the high voltage is applied to between the reactive reagent reservoir 11 and the waste solution reservoir 27 of the quantitative measuring device 2, is circulated in the form of an electroosmotic flow caused by the high voltage application through the passages 7b, 7c, 7d and 7e sequentially in this order.

The flows of the above eluting and reactive reagent solutions can be controlled with use of the passage change-over switches 13, 14 and 15. Their flow rate can be easily set by controlling the applied voltage. In more detail, the power change-over switch 6 acts to select the voltage application between the solution reservoir 9 and the waste solution reservoir 27 of the quantitative measuring device 2 or the voltage application between the reactive reagent reservoir 11 and the waste solution reservoir 27 of the quantitative measuring device 2. By controlling the applied voltage and the switching time, the amount of reactive reagent introduced into the passages can be readily adjusted. In this connection, each of the passages 7a to 7e was made up of a glass capillary tube (manufactured by GL Sciences company) having an inner diameter of 75 μm and an outer diameter of 375 μ m. Further, the passage change-over switches 13, 14 and 15 may be replaced, for example, by a three-way valve.

Sample introduction to the sample quantitative measurer 8 is carried out by means of the power supply 20 for sample introduction applying a high voltage between the platinum electrode 18 of the sample reservoir 17 placed on the sample stage 19 and the platinum electrode 22 of the waste solution reservoir 21. First of all, the automatic sample injector 16 is used to insert a tip end of the passage 7f into the sample reservoir 17 placed on the sample stage 19. Thereafter, the high voltage is applied between the platinum electrode 18 of the sample reservoir 17 and the platinum electrode 22 of the waste solution reservoir 21 so that the sample solution within the sample reservoir 17 flows in the form of an electroosmotic flow caused by the high voltage application through the passages 7f, 8 and 7g sequentially in this order. In this case, the amount of sample solution introduced can be set by the volume (internal volume) of the sample quantitative measurer 8. The tip end of the passage 7f and the platinum electrode 18 are assumed to be moved together by the sample stage with respect to the respective samples placed thereon.

Even when the sample quantitative measurer 8 is not used, the amount of sample solution introduced can be easily controlled by adjusting the applied voltage and application time. More specifically, the amount can be controlled by suitably switching the passage change-over switches 14 and 15 so as to communicate with the passages 7f, 7d and 7g, and adjusting the magnitude and application time of the high voltage applied from the power supply for sample introduction 20 to the platinum electrodes 18 and 22.

Thereafter, the introduced sample solution is sent through the passage 7e to the constant-temperature reservoir 24, made to react within the reactor 23 of the reservoir 24 with the reactive reagent sent from the reactive reagent reservoir 11, and then sent to the quantitative measuring device 2. In this case, the constant-temperature reservoir 24 is kept at an optimum temperature for the reaction.

The quantitative measuring device 2 includes a passage change-over unit 25, the reacted sample quantitative measurer 26, the waste reactive solution reservoir 27 and the platinum electrode 28 and functions to perform a quantitative measuring operation over the reaction sample subjected to the reaction at the micro-reactor device 1 and then to supply the quantitative-measured sample to the analyzing device 3.

The analyzing device 3 as a capillary electro-phoresis device in the present embodiment includes a capillary tube 29, a buffer reservoir 30, a buffer waste solution reservoir 33, platinum electrodes 31 and 33, a power supply for analysis 32, an optical detector 35 and a recorder 36. In this case, used as the capillary tube was a glass capillary tube (manufactured by GL Sciences company) having an inner diameter of 75 μm and an outer diameter of 375 μm.

First of all, the power supply for analysis 32 is used to apply a high voltage between the platinum electrode 31 of the buffer reservoir 30 and the platinum electrode 34 of the buffer waste solution reservoir 33 to thereby provide preliminary electrophoresis to solution and to keep the solution in such an electrophoresis enable state. After that, the reacted sample within the reacted sample quantitative measurer 26 of the quantitative measuring device 2 is introduced into the capillary tube 29 for electrophoresis. Components of the reacted sample separated within the capillary tube 29 by the electrophoresis are detected by the optical detector 35, and the migration times and concentration values for the respective detected components are sent to the recorder 36 to be recorded therein.

Although the capillary electrophoresis device has been used as the analyzing device in the present embodiment, a high performance liquid chromatography device may be employed in place of the capillary electrophoresis device while not compelling great modification in the device arrangement.

Further, since such operations as mentioned above are controlled by the controller 4, when the applied voltage and time, the power change-over timing, the passage change-over timing, etc. are controlled in the form of a computer program, this control can be carried out with use of a single switch.

The detailed procedure of a change-over method between the solution and reactive reagent will be explained by referring to FIG. 4 showing a part of the micro-reactor device 1 in FIG. 1.

Figure 4A:
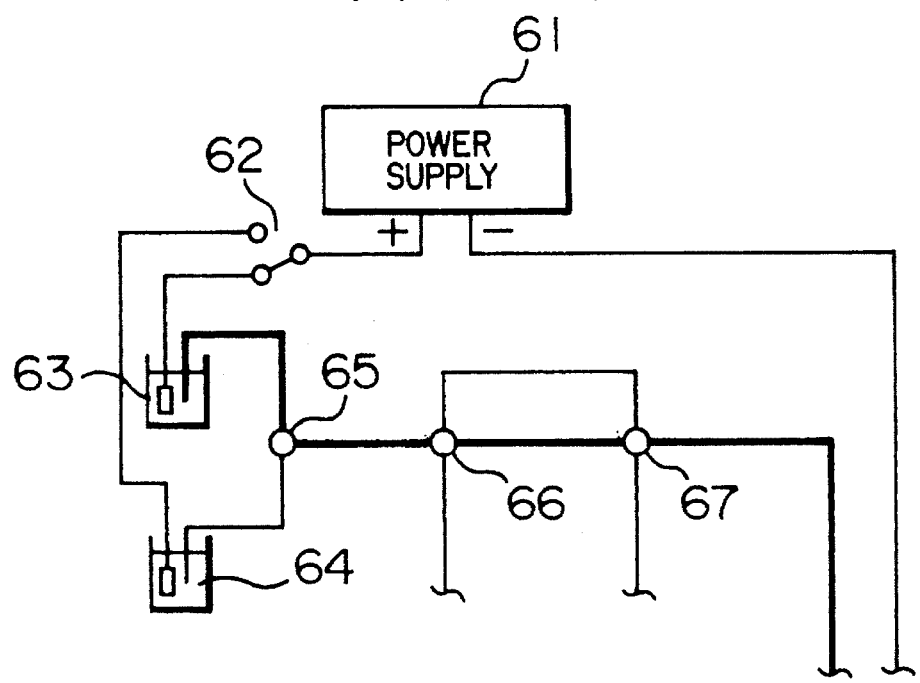
FIGS. 4A and 4B show detailed steps in a reagent introduction method.
Figure 4B:
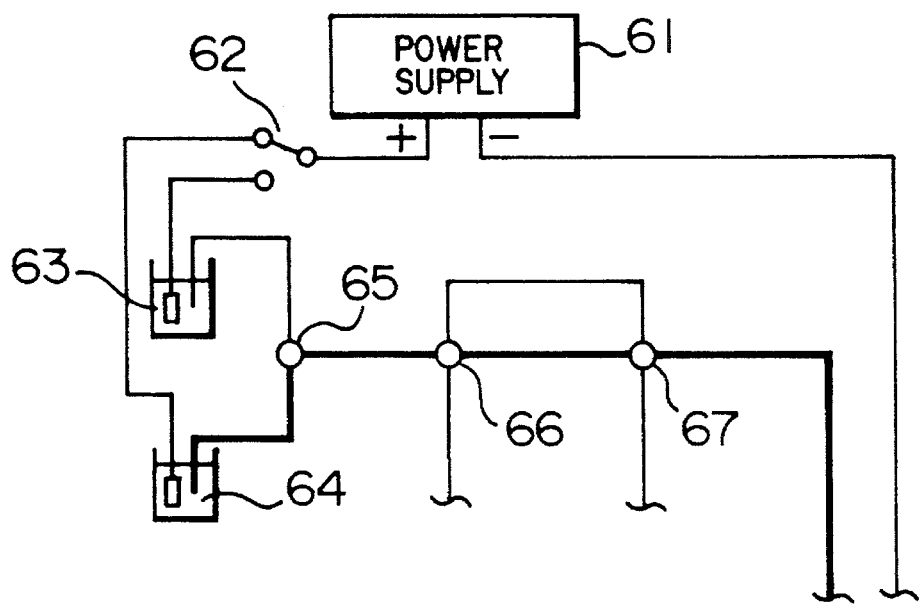

First of all, when it is desired to supply the solution, a power supply 61 for sample introduction is operated to apply a high voltage to a solution reservoir 63, in which case a power change-over switch 62, operatively connected with a passage change-over switch 65, is set at such a position as to form a thick solid line passage shown in FIG. 4A. Next, when it is desired to supply the reactive reagent, the power change-over switch 62 is switched to the other position so that, at the same time that a high voltage is applied to a reactive reagent reservoir 64, the passage change-over switch 65 operatively connected with the power change-over switch 62 is also switched, whereby such a path as shown by a thick solid line in FIG. 4B is established. In this case, passage change-over switches 66 and 67 are operatively connected with the power supply for sample introduction 61, so that, when it is desired to supply the solution by means of the power supply for sample introduction 61, such a path as shown by a thick solid line in FIG. 4B is formed.

The detailed procedures of a sample introducing method and a reaction method between the sample and reactive reagent will be explained by referring to FIG. 5 showing a part of the micro-device 1 in FIG. 1.

Figure 5A:
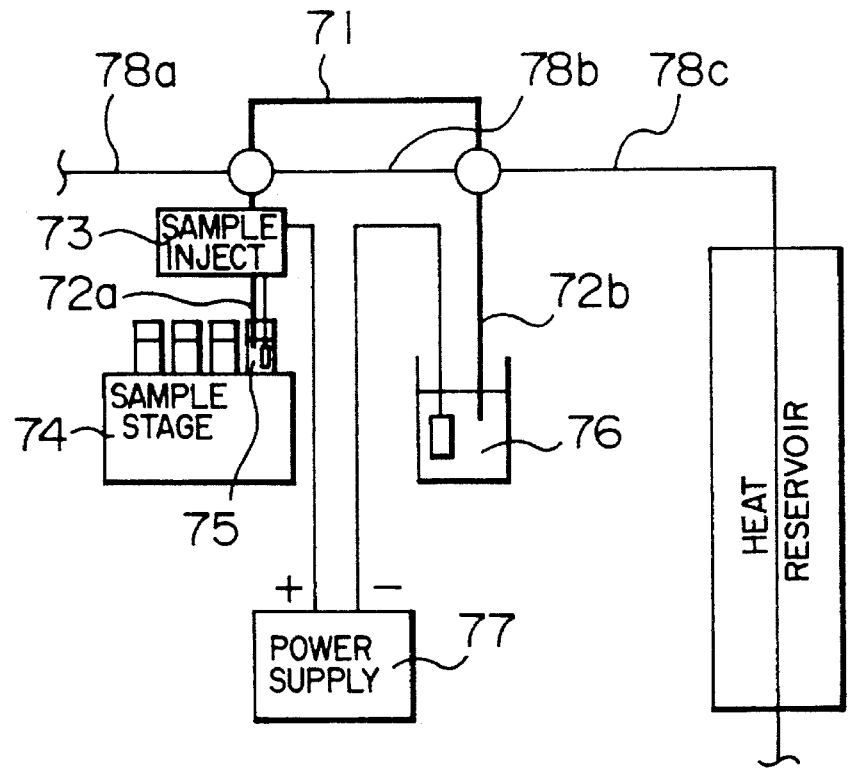
FIGS. 5A, 5B and 5C show detailed steps in a sample introduction method and in a sample-reagent reaction method.
Figure 5B:
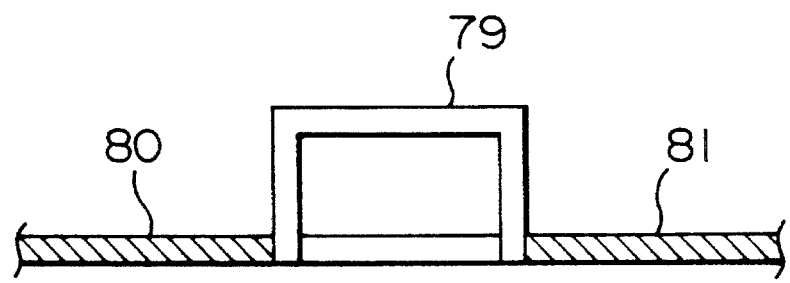
Figure 5C:
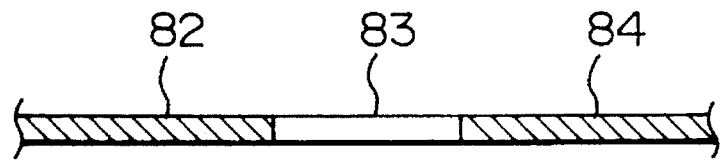

When it is desired to introduce the sample as shown in FIG. 5A, an automatic sample injector 73 is operated to insert a tip end of a passage 72a into a sample reservoir 75 placed on a sample stage 74, and then a power supply 77 for sample introduction is operated to apply a high voltage to between the sample and waste solution reservoirs 75 and 76. Application of the high voltage to the sample and waste solution reservoirs 75 and 76 causes generation of an electroosmotic flow, whereby the sample solution within the sample reservoir 75 flows through passages 72a, 71 and 72b sequentially in this order. At this time, the reactive reagent is also being supplied through passages 78a, 78b and 78c sequentially in this order. In other words, as shown in FIG. 5B, there are reactive reagents 80 and 81 at upstream and downstream or front and rear ends of a sample 79, that is, the sample is put in a sandwiched relation between the reactive reagents 80 and 81. Thereafter, supply of the solution by the electroosmotic flow causes the sample and reagents to flow while reacting with one another as shown in FIG. 5C. Further, since the sample 83 is put in the sandwiched relation between the reactive reagents 82 and 84 to be efficiently mixed with the reactive reagents 82 and 84 at the front and rear ends of the sample 83 through diffusion, the efficient reaction can be realized. As already explained above, the passage change-over switches 66 and 67, when it is desired to supply the solution by means of the operation of the power supply for sample introduction 61, are set at such positions as to form the path shown by the thick solid line in FIG. 4B. However, when it is desired to introduce the sample, power change-over to the power supply for sample introduction 77 causes change-over of the passage change-over switches 66 and 67, with the result that such a path as shown by a thick solid line in FIG. 5A is formed.

Explanation will be made as to the more detailed procedure of a method for analyzing the reactive sample in connection with FIG. 6 showing a part of the quantitative measuring device 2 and analyzing device 3 in FIG. 1.

Figure 6A:
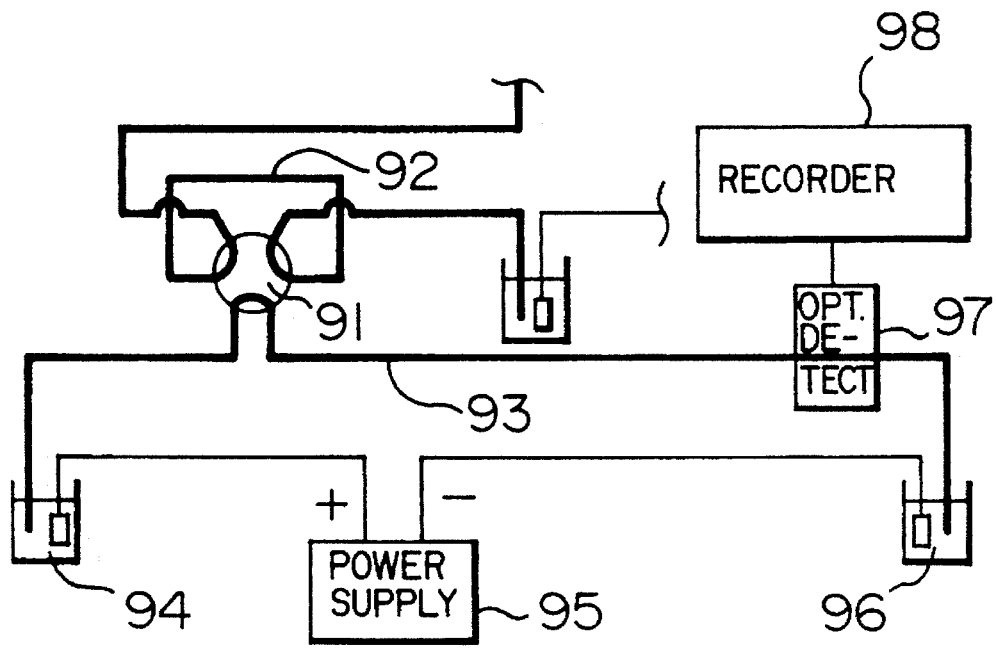
FIGS. 6A and 6B show detailed steps in an analysis method.
Figure 6B:
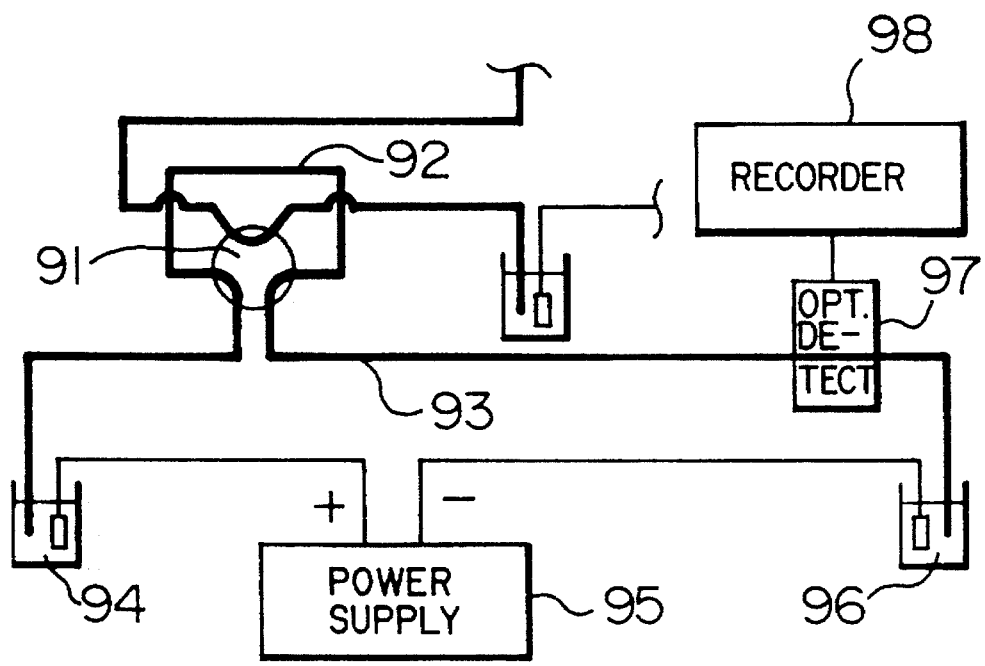

First, for the purpose of providing preliminary electrophoresis, a power supply for analysis 95 is operated apply a high voltage to between a buffer reservoir 94 and a buffer waste solution reservoir 96. At this time, as shown in FIG. 6A, the reacted sample supplied from the micro-reactor device 1 is filled within a reacted sample quantitative measurer 92 of a passage change-over switch 91. Thereafter, the passage change-over switch 91 is switched so that the reacted sample is introduced into a capillary tube 93 for electrophoresis as shown by a thick solid line in FIG. 6B. In this connection, the passage change-over switch 91 is operatively connected with an optical detector 97 and a recorder 98 so that change-over of the switch 91 causes simultaneous analysis and recording of the sample thereat.

Since the transfer of the sample and reactive reagent is based on electroosmotic flow in the present embodiment, the diffusion of the sample and reactive reagent is as small as several tenths of that in the case of laminar flow. Further, substantially no pressure drop can be caused by the solution transfer, and the reaction between a very small amount of sample and reactive reagent can be efficiently carried out within a capillary tube as small as 100 μm or less in inner diameter. Furthermore, since the micro-reactor device is connected via the measuring device to the capillary electrophoresis device, a very small amount of sample can be accurately introduced into the capillary electro-phoresis device, and on-line analysis including reaction of the very small amount of sample with the reagent and separation of sample composition can be performed without involving any dilution and loss of the sample.

In the foregoing embodiment, explanation has been made in connection with such a system that is an integral combination of the micro-reactor device, measuring device and capillary electrophoresis device. Thus, when the micro-reactor device alone is extracted from the system, one terminal for supplying power to provide electroosmotic flow is missing in the micro-reactor device, but as this problem can be solved by providing a reservoir corresponding to the waste solution reservoir 27 of the quantitative measuring device 2 to the micro-reactor device.

Figure 7:
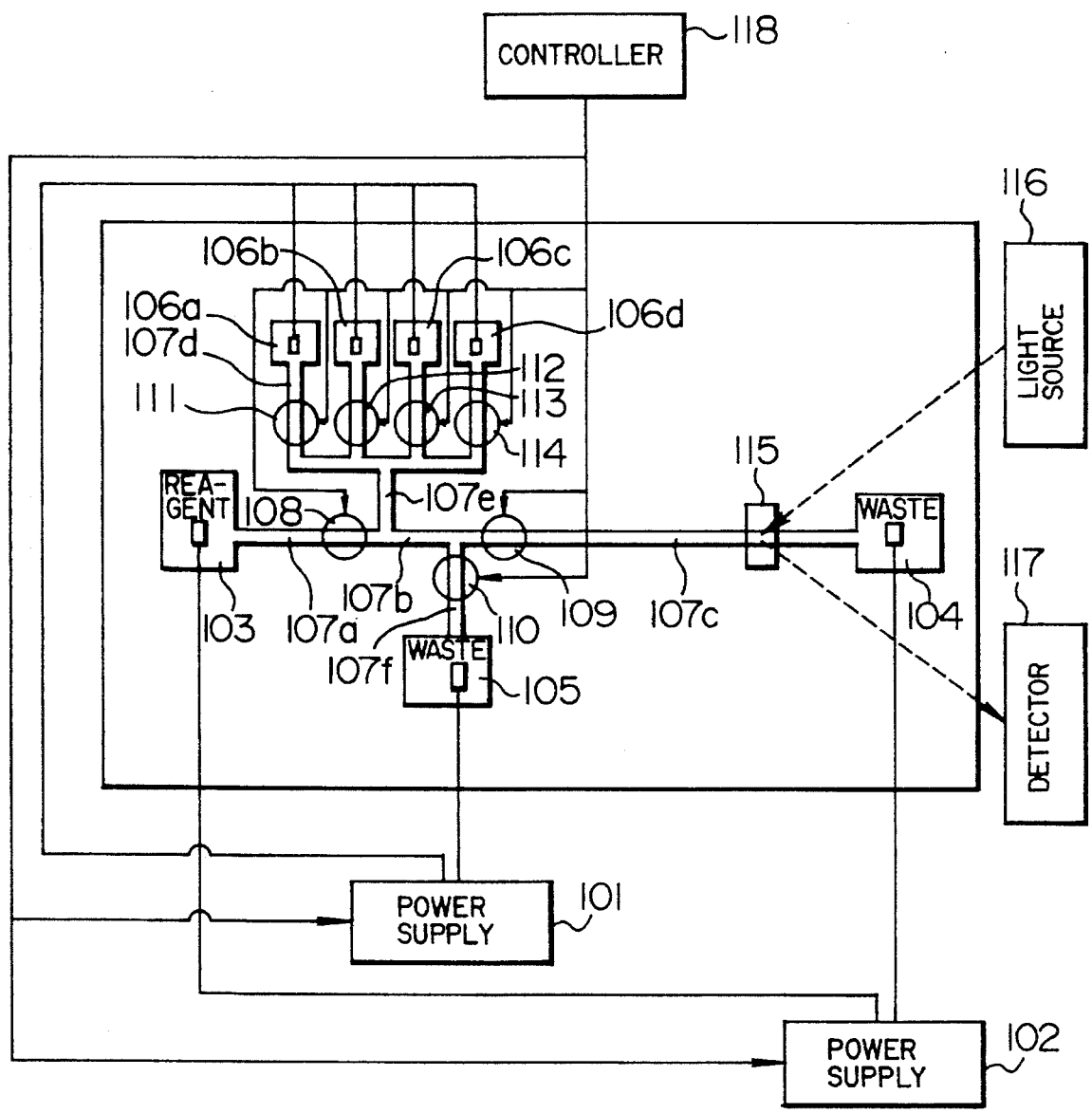
FIG. 7 is a block diagram of an arrangement of a second micro-reactor device in accordance with the present invention.

Explanation will be made as to a micro-reactor device in accordance with a second embodiment of the present invention by referring to FIG. 7 showing its block diagram.

The illustrated micro-reactor device of the second embodiment includes power supplies 101 and 102, a reactive reagent reservoir 103, waste solution reservoirs 104 and 105, sample reservoirs 106a to 106d, passages 107a to 107f, passage change-over switches 108, 109, 110, 111, 112, 113 and 114, a measurer 115, a light source 116, a detector 117, and a controller 118. The micro-reactor device except the power supplies is formed on a planar plate insulator such as a glass plate, a single crystal silicone substrate, etc.

In more detail, the power supply 102 having a high output voltage of 0–30 kV is used to apply a high voltage between an electrode of the reactive reagent reservoir 103 and an electrode of the waste solution reservoir 104. The power supply 101 is used to apply a high voltage between electrodes of the sample reservoirs 106a to 106d and an electrode of the waste solution reservoir 105.

When the high voltage is applied between the electrode of the reactive reagent reservoir 103 and the electrode of the waste solution reservoir 104, the electroosmotic flow generated by the high voltage application causes the reactive reagent within the reactive reagent reservoir 103 to flow through the passages 107a, 107b and 107c sequentially in this order. Similarly, when the high voltage is applied between the electrodes of the sample reservoirs 106a to 106d and the electrode of the waste solution reservoir 105, the electroosmotic flow generated by the high voltage application causes the sample solution within the sample reservoirs 106a to 106d to flow through the passages 107d, 107e, 107b and 107f sequentially in this order. In the illustrated example, the micro-reactor device is designed for selective application of 4 samples. The flows of the above reactive reagent and sample can be switchingly controlled by means of the passage change-over switches 108, 109, 110 and 111 based on a signal issued from the controller 118. In this connection, the flow rate can be easily set by adjusting the applied voltage or time of the power supplies 101 and 102 on the basis of a signal from the controller 118.

The reaction of the micro-reactor device of the present embodiment is carried out in the following sequence.

First of all, the reactive reagent is introduced into the passages 107a, 107b and 107c, at which time the passage change-over switches 110 and 111–114 are operated to close the path and to stop the flowing of the sample. Subsequently, a high voltage is applied to between the electrode of the reactive reagent reservoir 103 and the electrode of the waste solution reservoir 104 so that the electroosmotic flow generated by the high voltage application causes the reactive reagent within the reactive reagent reservoir 103 to flow through the passages 107a, 107b and 107c sequentially in this order.

Thereafter, the passage change-over switches 108 and 109 are operated to close the path and to stop the flowing of the reactive reagent.

Next, when it is desired to introduce the sample into the passage 107b also functioning as a sample quantitative measurer, the power supply 101 for sample injection is operated to apply a high voltage between the electrode of the sample reservoir 106a and the electrode of the waste solution reservoir 105.

The passage change-over switches 110 and 111 are first operated to open the path. After that, a high voltage is applied to between the electrode of the sample reservoir 106a and the electrode of the waste solution reservoir 105 so that the electroosmotic flow generated by the high voltage application causes the sample within the sample reservoir 106a to flow through the passages 107d, 107e, 107b and 107f sequentially in this order. In this conjunction, the amount of sample introduced can be set by the capacity of the passage 107b functioning also as a sample quantitative measurer. Even with respect to the sample solutions of the sample reservoirs 106b to 106d, the sample introduction can be similarly controlled by the passage change-over switches 112, 113 and 114.

With respect to the introduced sample and reactive reagent, the passage change-over switches 110 and 111 are operated to close the path and to stop the flowing of the sample and subsequently the passage change-over switches 108 and 109 are operated to open the reactive reagent path. Under this condition, when the high voltage is applied between the electrode of the reactive reagent reservoir 103 and the electrode of the waste solution reservoir 104, the electroosmotic flow generated by the high voltage application causes the sample and reactive reagent to flow through the passages 107b and 107c while reacting with each other. Thus, there are reactive reagents at the front and rear ends of the sample introduced into the passage 107b, that is, the sample is put in a relationship sandwiched between the reactive reagents. Thereafter, the solution transfer based on the electroosmotic flow causes the sample and reactive reagent to react with each other while flowing. At this time, since the sample is sandwiched between the reactive reagents, the sample can be efficiently mixed with the reactive reagents at the front and rear ends thereof through diffusion for efficient reaction there-between. When the optimum temperature of the reaction is high, temperatures in the passages 107b and 107c can be set at proper levels for reaction without any troubles.

After that, light from the light source 116 is directed to the reacted sample. Change of light intensity due to the reacted sample is detected by the detector 117 to measure a sample quantity. In this connection, the change of light intensity means absorbance, fluorescence intensity, etc. Thus, the measurer 115 has a high light transmittance, and especially in case of absorbance change measurement, the measurer passage is provided thereon with a light reflecting layer to prolong its light path length. Further, when it is desired to measure a multiplicity of samples, this can be easily realized by sequentially operating the passage change-over switches 111, 112, 113 and 114 in similar procedures to the above.

The aforementioned operations are controlled by the controller 118, and thus when the applied voltage and time, passage change-over timing, etc. are controlled in accordance with a computer program, the operation control can be realized with use of a single switch.

More detailed explanation will be made as to the passage arrangement of the aforementioned micro-reactor device by referring to FIG. 8.

Figure 8A:
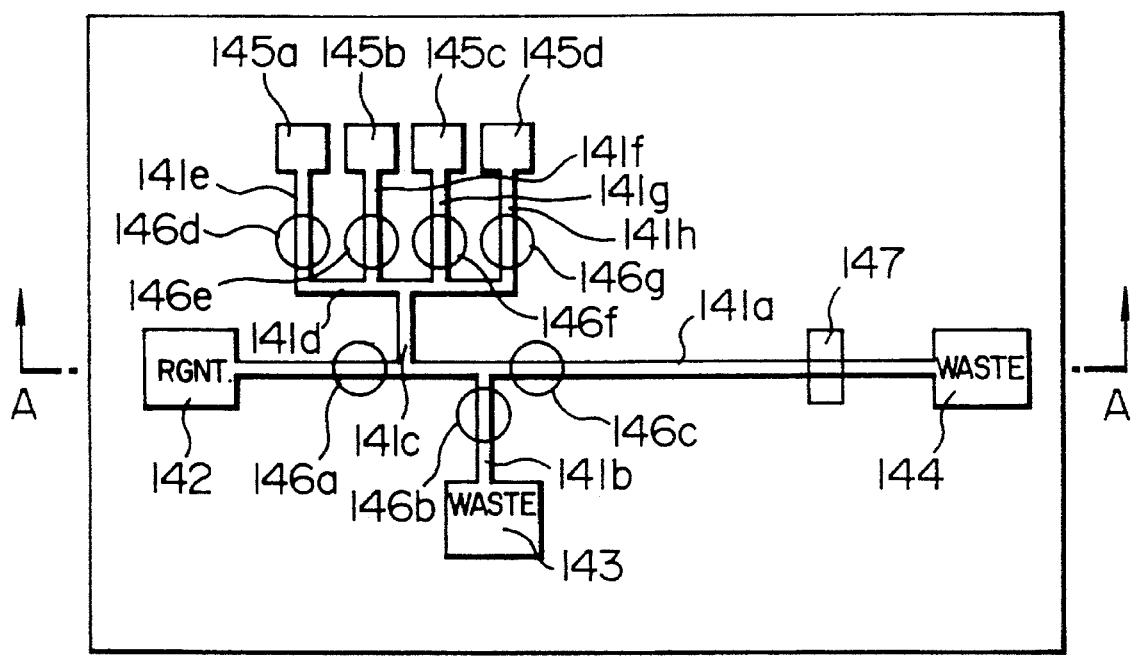
FIGS. 8A and 8B show a structure of flow passages of the second micro-reactor device.

FIG. 8A shows a passage arrangement of the micro-reactor device. The passages of the micro-reactor device are formed by first providing very narrow grooves and small through holes in such a planar substrate as a glass or silicon substrate, overlapping another planar substrate on the former substrate, and then joining the substrates together by fusion bonding. As a result, passages 141a to 141h are defined by the very narrow grooves, while a reactive reagent reservoir 142, waste solution reservoirs 143 and 144, and sample reservoirs 145a to 145d are defined by the small through holes. The formation of the very small grooves and small through holes may be effected by mechanical machining with use of a drill or by chemical treatment such as etching. Further, passage change-over switches 146a to 146g may function to perform their switching operation by mechanically opening or closing the small through holes for passage change-over or by partially freezing or unfreezing the passages 141a to 141h.

Figure 8B:
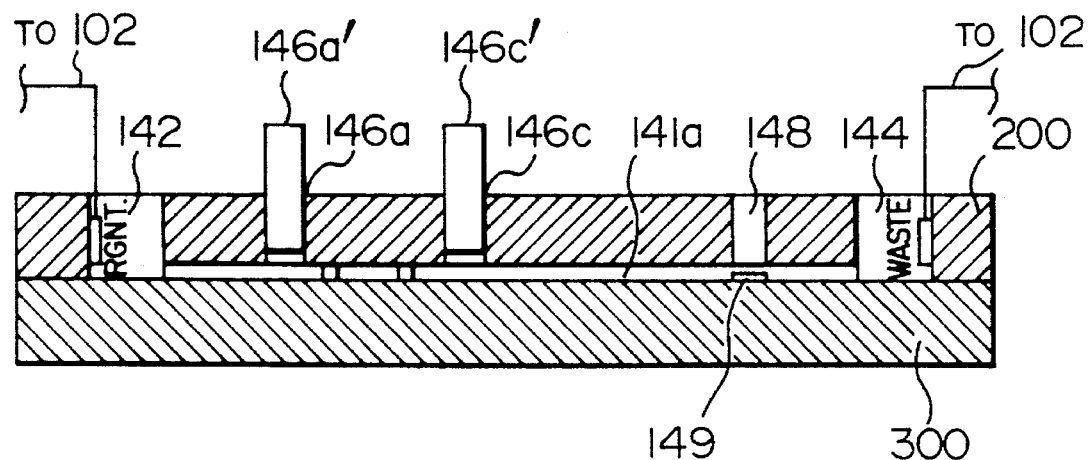

FIG. 8B shows a side cross-sectional view of the micro-reactor device of FIG. 8A as viewed from a passage position A—A shown by arrows. In the drawing, reference numeral 200 denotes a planar substrate which is provided in its one surface with very small grooves and small through holes. Numeral 300 denotes a planar substrate overlapped on the substrate 200. The passage change-over switches 146a and 146c are provided therein with members 146a' and 146c' which function as stop plugs and, as already explained above, which are controlled by the controller 118 to open or close the associated passages. Further, the reactive reagent reservoir 142, waste solution reservoirs 143 and 144, and sample reservoirs 145a to 145d are provided on their walls with electrodes for providing electroosmotic flow (only two of which electrodes, for the reactive reagent reservoir 142 and the waste solution reservoir 144, being illustrated in the drawing).

Since the reactive reagent reservoir 142, waste solution reservoirs 143 and 144, and sample reservoirs 145a to 145d are provided in the same planar substrate in the present embodiment, the need for connecting the reactive reagent reservoir, waste solution reservoirs and sample reservoirs through connectors as in the prior art can be eliminated, and thus a leakage problem and the need for interconnections in very small areas can be removed. Further, since only the controller, high voltage power supplies and optical detector are provided as external devices, the entire apparatus can be made easily small in size.

Furthermore, since the reactive reagent reservoir 142, waste solution reservoirs 143 and 144, and sample reservoirs 145*a* to 145*d* are disposed as externally faced, introduction and the exchange of the reactive reagent and sample, washing, and waste solution removing can be facilitated. In this connection, the amounts of reactive reagent and sample used depend on the sizes of the reactive reagent reservoir and sample reservoirs. For this reason, minute amount of sample, as small as the microliter level, can be exchanged without any loss by making the diameter of the small through holes for the reactive reagent reservoir and sample reservoirs to be below 5000 µm. A measurer 147 includes a light transmittable part 148, made of silica glass having a high light transmittance, and a light reflecting layer 149. The light reflecting layer 149 is made preferably of material having an excellent reflectance such as platinum or rhodium. When it is desirable to provide the measurer in the form of a light transmission type, the reflecting layer 149 can be omitted.

Explanation will be made as to an example of the structure of a passage change-over means by referring to FIG. 9.

Figure 9A:
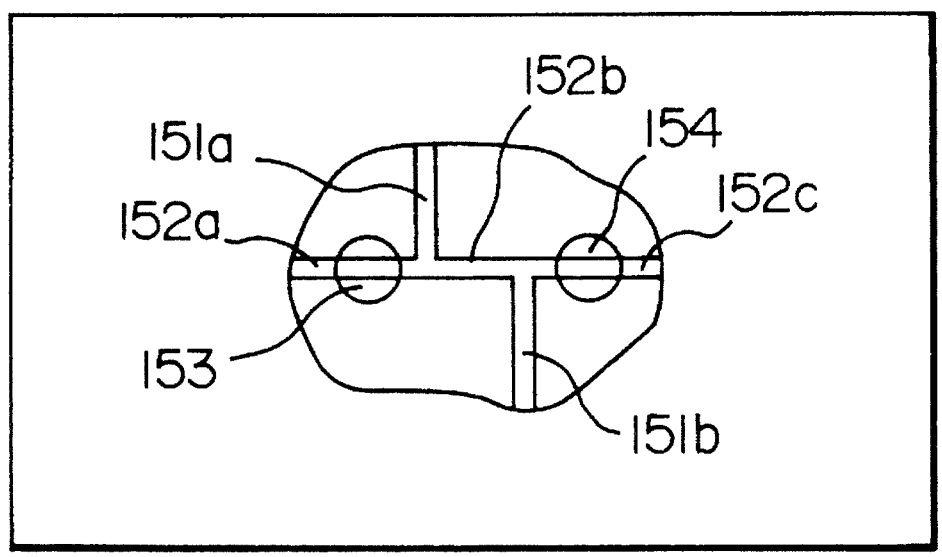
FIGS. 9A and 9B show a structure of a passage switching part in the second micro-reactor device.
Figure 9B:
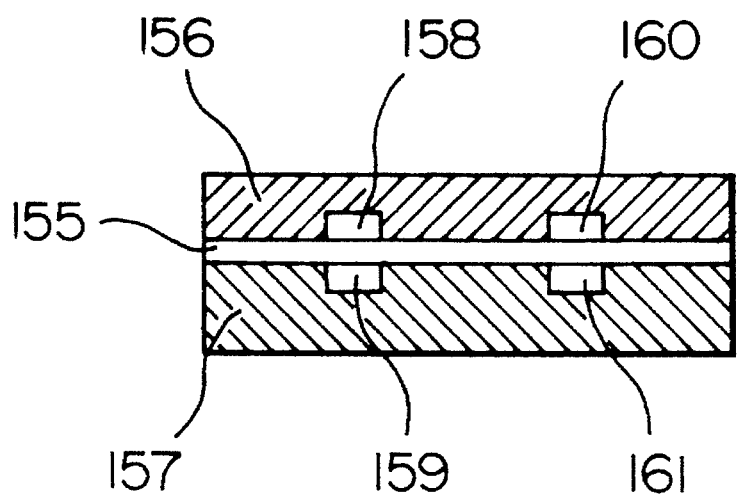

FIG. 9A shows a part of the passage change-over means which includes sample passages 151*a* and 151*b*, reactive reagent passages 152*a* to 152*c* and passage change-over switches 153 and 154. In this case, the passage 152*b* functions also as a sample quantitative measurer. The sample quantitative measurement and reaction can be carried out by closing the passage change-over switches 153 and 154 to introduce the sample into the passage 152*b* functioning also as the sample quantitative measurer. FIG. 9B shows a side cross-sectional view of a part of a passage change-over means which includes Peltier elements 158, 159, 160 and 161 which are made in planar substrates 156 and 157, as opposed to each other with a passage 155 disposed therebetween. Passage change-over can be effected by cooling the solution in the passage to −15° C. or less by means of the Peltier elements 158, 159, 160 and 161 to close the passage 155.

According to the present embodiment, the passage change-over in microscopic areas can be facilitated with a simple arrangement because the opening and closing of the passages is carried out by freezing and unfreezing the solution in the passages.

What is claimed is:

1. A micro-reactor device for causing a reaction between a sample and a reagent, said device comprising:

a sample reservoir for holding a sample;

a reagent reservoir for holding a reagent;

a first waster reservoir for holding a first waste solution;

a second waste reservoir for holding a second waste solution;

means defining a first passage connecting said reagent reservoir and said first waster reservoir;

a first passage switch in said first passage, for controlling flow therethrough;

a second passage switch in said first passage, intermediate said first passage switch and said first waster reservoir, for controlling flow therethrough;

means defining a second passage connecting said sample reservoir and said first passage at a first junction intermediate said first and second passage switches;

a third passage switch in said second passage, for controlling flow therethrough;

means defining a third passage connecting said second waster reservoir and said first passage at a second junction intermediate said first and second passage switches;

a fourth passage switch in said third passage, for controlling flow therethrough;

generating means for applying a voltage to said passage to cause electroosomotic flow of fluids in said passages; and a controller for controlling said passage switches and said generating means, to cause elecroosomotic flow of reagent in said first passage followed by electroosomotic flow of a predetermined volume of sample in said first sample passage between the first junction ad the second junction and then electroosomotic flow of reagent in said first passage.

2. A micro-reactor device as claimed in claim 1, wherein:

a first planar insulator substrate and a second planar insulator substrate are provided, the first planar insulator substrate having a bonding surface and the second planar insulator substrate having a bonding surface bonded to the bonding surface of said first planar insulator substrate;

one of said planar insulator substrates has first, second, third, and fourth openings therethrough to provide, respectively, the sample reservoir, the reagent reservoir, the first waste reservoir, and the second waste reservoir; and one of said bonding surfaces has first, second and third grooves formed therein to define, respectively, the first passage, the second passage, and the third passage.

3. A micro-reactor device as claimed in claim 1, further comprising an optical measuring device, including a measuring chamber within said first passage at a point intermediate said second passage switch and said first waster reservoir, a light source for radiating light into said measuring chamber for reflection, and a light detector for detecting light reflected from said measuring chamber to detect fluids therein.

4. A micro-reactor device as claimed in claim 1, wherein said generating means comprises:

first, second, third, and fourth electrodes positioned, respectively, in said sample reservoir, in said reagent reservoir, in said first waste reservoir, and in said second waste reservoir;

a first power supply for supplying voltage between said second and third electrodes; and a second power supply for supplying voltage between said first and fourth electrodes.

5. A micro-reactor device as claimed in claim 1, wherein each of said grooves has a diameter of 100 µm or less.

6. A micro-reactor device as claimed in claim 3, wherein said measuring chamber comprises a light transmitting portion in one of said substrates for transmitting light to said first passage and a light reflector in said first passage for reflecting the light transmitted by said light transmitting portion.

7. A micro-reactor device for causing a reaction between a sample and a reagent, said device comprising:

a first planar insulator substrate having a bonding surface;

a second planar insulator substrate having a bonding surface bonded to the bonding surface of said first planar insulator substrate, one of said planar insulator substrates having first, second, third, and fourth openings therethrough to provide, respectively, a sample reservoir, a reagent reservoir, a first waste reservoir, and a second waste reservoir, and one of said bonding surfaces having first, second and third grooves formed therein to provide, respectively, a first passage connecting said reagent reservoir and said first waste reservoir, a second passage connecting said sample reservoir and said first passage, and a third passage connecting said second waster reservoir and said first passage;

first, second, third, and fourth electrodes positioned, respectively, in said sample reservoir, in said reagent reservoir, in said first waste reservoir, and in said second waster reservoir;

a first passage switch in said first passage, intermediate said reagent reservoir and said second and third passages, for controlling flow therethrough;

a second passage switch in said first passage, intermediate said second and third passages and said first waste reservoir, for controlling flow therethrough;

a third passage switch in said second passage, for controlling flow therethrough;

a fourth passage switch in said third passage, for controlling flow therethrough;

an optical measuring device, including a measuring chamber within said first passage at a point intermediate said second passage switch and said first waste reservoir, a light source for radiating light into said measuring chamber for reflection, and a light detector for detecting light reflected from said measuring chamber to detect fluids therein;

a first power supply for supplying voltage between said second and third electrodes;

a second power supply for supplying voltage between said first and fourth electrodes; and a controller for controlling said passage switches and said power supplies, to control flow between said reservoirs through said passages.

8. A micro-reactor device as claimed in claim 7, wherein each of said grooves has a diameter of 100 μm or less.

9. A micro-reactor device as claimed in claim 7, wherein each of said passage switches controls flow by freezing and unfreezing an adjacent part of the passage.

10. A micro-reactor device as claimed in claim 7, wherein each of said passage switches comprises a plug for plugging the passage.

11. A micro-reactor device as claimed in claim 7, wherein said measuring chamber comprises a light transmitting portion in one of said planar insulator substrates for transmitting light to said first passage and a light reflector in said first passage for reflecting the light transmitted by said light transmitting portion.

* * * * *